US00PP19472P3

(12) United States Plant Patent
Shaw et al.

(10) Patent No.: US PP19,472 P3
(45) Date of Patent: Nov. 25, 2008

(54) STRAWBERRY PLANT NAMED 'PALOMAR'

(50) Latin Name: *Fragaria×ananassa*
Varietal Denomination: Palomar

(75) Inventors: Douglas V. Shaw, Davis, CA (US); Kirk D. Larson, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/654,204

(22) Filed: Jan. 16, 2007

(65) Prior Publication Data

US 2008/0184408 P1 Jul. 31, 2008

(51) Int. Cl.
*A01H 5/00* (2006.01)

(52) U.S. Cl. ..... Plt./208; Plt./209

(58) Field of Classification Search ..... Plt./208, Plt./209

See application file for complete search history.

*Primary Examiner*—Anne Marie Grunberg
*Assistant Examiner*—S. B. McCormick-Ewoldt
(74) *Attorney, Agent, or Firm*—Townsend and Townsend and Crew LLP

(57) ABSTRACT

This invention relates to a new and distinctive short-day type cultivar designated as 'Palomar'. 'Palomar' is a short-day (June-bearing) cultivar similar to 'Camino Real' (U.S. Plant Pat. No. 13,079), but with higher quality fruit, lower cull rate and lighter colored fruit; it is similar to 'Ventana' (U.S. Plant Pat. No. 13,469), but with a more compact plant, superior fruit quality, and firmer, better flavored fruit.

4 Drawing Sheets

Genus and species: The strawberry cultivar of this invention is botanically identified as *Fragaria×ananassa* Duch.

Variety denomination: The variety denomination is 'Palomar'.

BACKGROUND OF THE INVENTION

'Palomar' originated from a cross performed in 2000 between the cultivars 'Camino Real' (U.S. Plant Pat. No. 13,079) and 'Ventana' (U.S. Plant Pat. No. 13,469). Because 'Palomar' was isolated from pooled seed from a reciprocal cross, it is not known which parent is the maternal parent and which is the paternal parent. 'Palomar' was first fruited near Winters, Calif. in 2001, where it was selected, originally designated Cal 0.259-2, and propagated asexually by runners. Following selection and during testing, the plant was designated 'C221'. Asexual propagules from this original source have been tested in Watsonville, Calif., Irvine, Calif., and to a limited extent in grower fields starting in 2002. The properties of this variety were found to be transmissible by such asexual reproduction. The cultivar is stable and reproduces true to type in successive generations of asexual reproduction.

BRIEF SUMMARY OF THE INVENTION

This invention relates to a new and distinctive short-day type cultivar designated as 'Palomar'. 'Palomar' is a short-day (June bearing) cultivar similar to 'Camino Real' (U.S. Plant Pat. No. 13,079) but with higher quality fruit, lower cull rate and lighter colored fruit; it is similar to 'Ventana' (U.S. Plant Pat. No. 13,469) but with a more compact plant, superior fruit quality, and firmer, better flavored fruit.

BRIEF DESCRIPTION OF THE DRAWINGS

The figures depict various characteristics of the 'Palomar' cultivar.

DETAILED DESCRIPTION OF THE INVENTION

Figure 1:
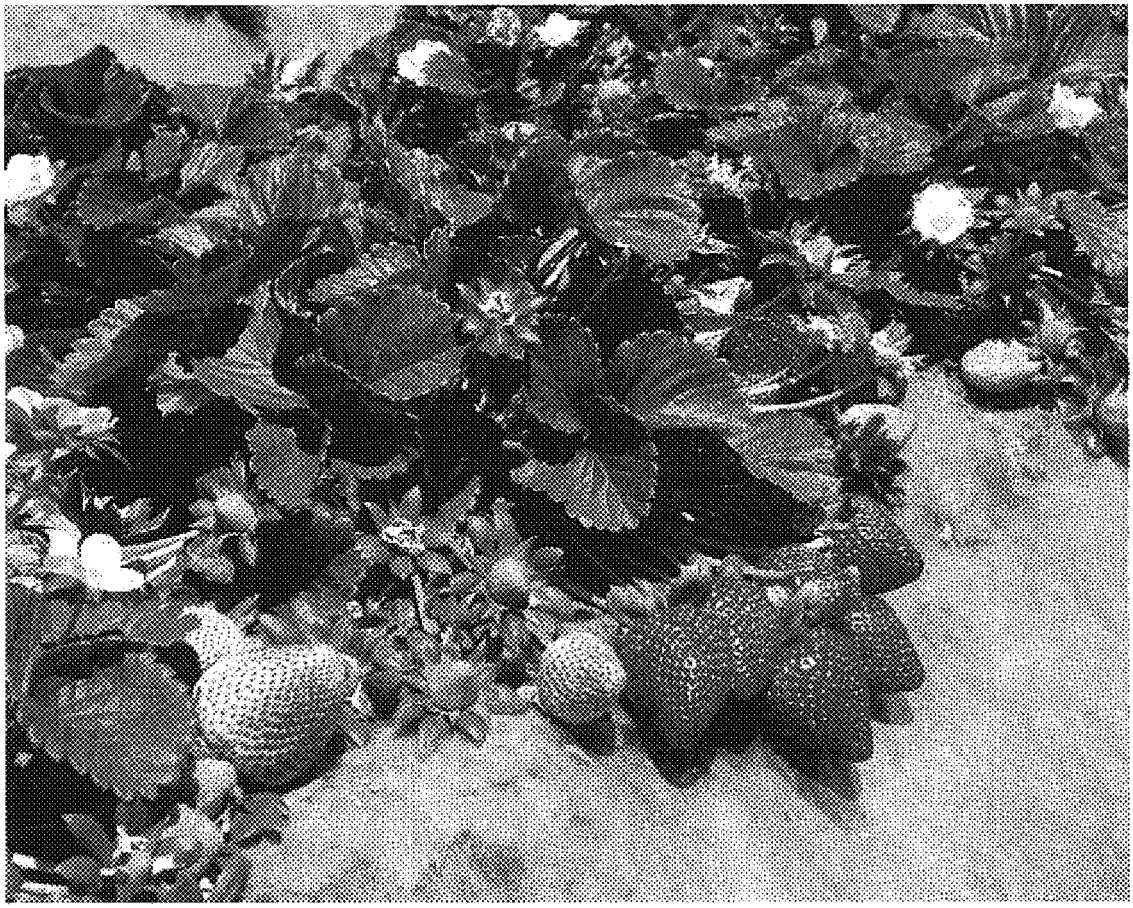
FIG. 1 shows the general flowering and fruiting characteristics of plants in a field planting.
Figure 2:
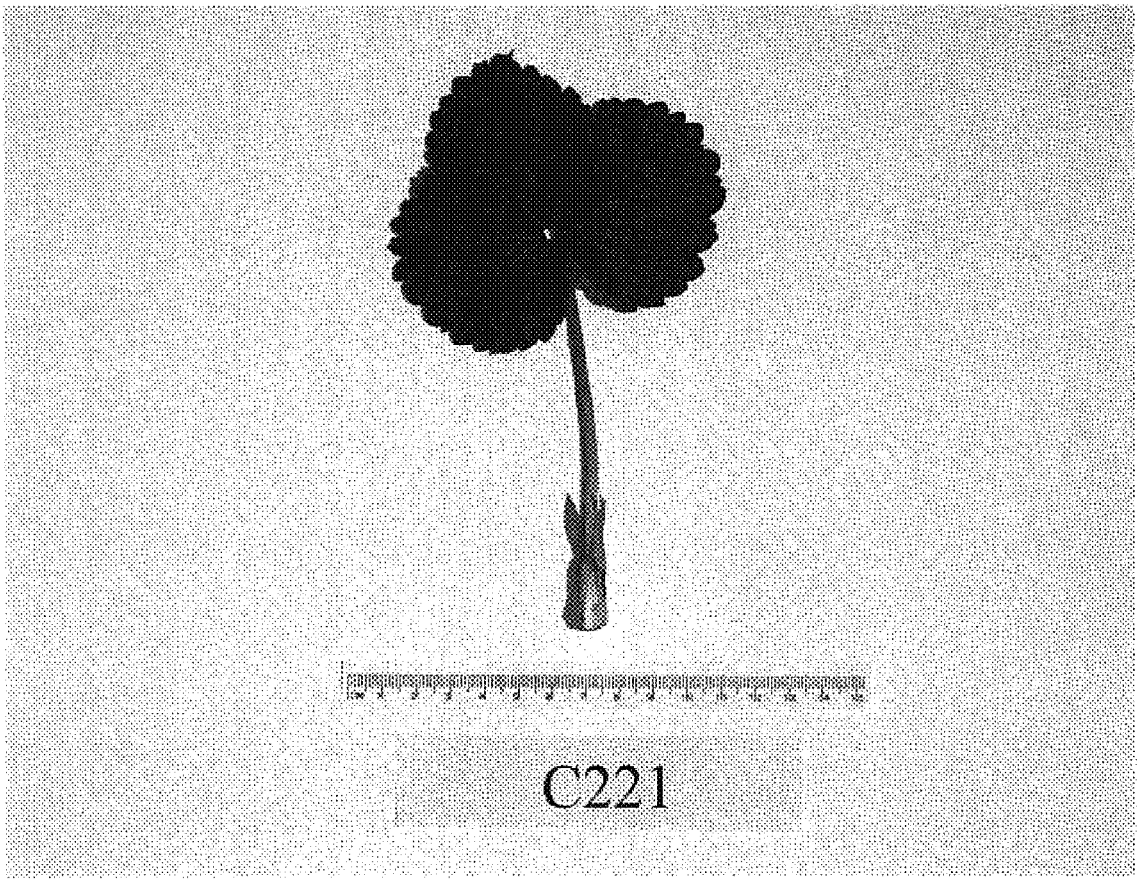
FIG. 2 shows a typical leaf at mid-season.
Figure 3:
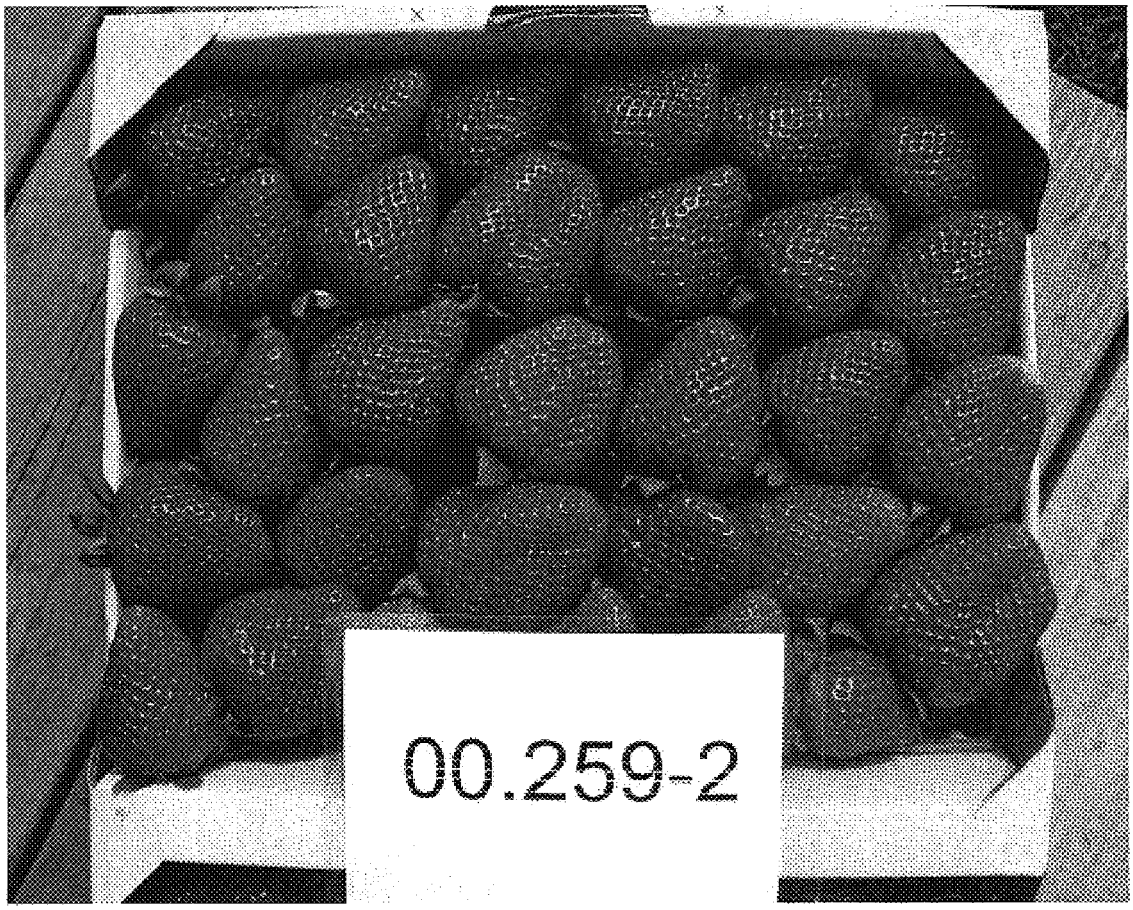
FIG. 3 shows representative mid-season fruit.
Figure 4:
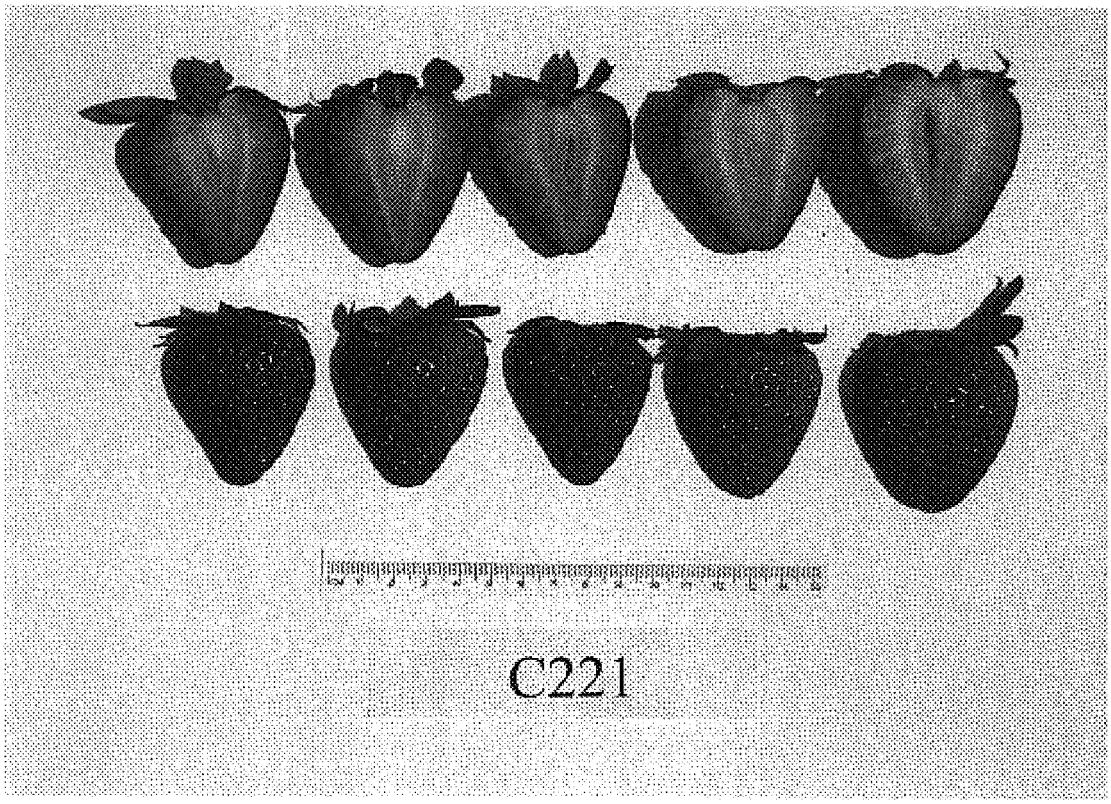
FIG. 4 shows a cross-section of representative mid-season fruit.

This invention relates to a new and distinctive short-day type cultivar designated as 'Palomar'. 'Palomar' is typical of short-day strawberry cultivars and produces fruit over an extended period when treated appropriately in arid, subtropical climates. The production pattern for 'Palomar' is similar to that for 'Camarosa' (U.S. Plant Pat. No. 8,708) and 'Camino Real' (U.S. Plant Pat. No. 13,079), although it is somewhat earlier to initiate fruiting with most cultural treatments. 'Palomar' initiates fruiting somewhat earlier than 'Ventana' (U.S. Plant Pat. No. 13,469) when established in very early fall and somewhat later than 'Ventana' when established in mid to late fall. 'Palomar' will be of special interest for winter plantings, where 'Camarosa', 'Ventana' and 'Camino Real' have been successful, and in summer plantings where 'Pajaro' (U.S. Plant Pat. No. 4,538) and 'Chandler' (U.S. Plant Pat. No. 5,262) have been successful.

Plants and foliage: Fruiting plants of 'Palomar' are similar in morphology to 'Ventana' although slightly more erect and much smaller throughout most of the production season; 'Palomar' plants are slightly larger and less open than those of 'Camino Real' in most production environments. Comparative statistics for foliar characters near mid-season are given for 'Palomar' and three comparison cultivars in Table 1. Individual leaflets for 'Palomar' are smaller and less rounded than for 'Camarosa' or 'Camino Real', similar in shape to but smaller than for 'Ventana'. Leaves (including petioles) for 'Palomar' are shorter than those for the comparison cultivars, mostly due to shorter petiole length. Petioles for 'Palomar' are generally thicker than those of the comparison cultivars relative to their length and tend to have moderate or heavy pubescence. The adaxial (upper) and abaxial (lower) surfaces of leaves for 'Palomar' are similar in color to 'Camarosa' and lighter than for 'Camino Real' leaves at mid season; they tend to remain darker and less yellow than those for 'Ventana' late in the harvest season. Leaves of 'Palomar' have consistently more concavity than 'Camarosa', less concavity than 'Camino Real' and are similar to those for 'Ventana'. Serrations at mid season are more pointed than for 'Camarosa', similar in shape and number to 'Ventana' and 'Camino Real'.

TABLE 1

Foliar and plant characteristics for 'Palomar', 'Camarosa', 'Camino Real', and 'Ventana'.

| Foliar Character | Cultivar 'Camarosa' | 'Camino Real' | 'Ventana' | 'Palomar' |
|---|---|---|---|---|
| Plant height (mm) | | | | |
| mean | 254 | 249 | 271 | 196 |
| range | 203-279 | 229-279 | 254-292 | 152-229 |
| Plant spread (mm) | | | | |
| mean | 427 | 418 | 468 | 391 |
| range | 394-493 | 330-495 | 343-521 | 305-432 |
| Mid-tier leaflet Length (mm) | | | | |
| mean | 83.5 | 79.5 | 87.2 | 75.5 |
| range | 70-100 | 70-95 | 70-110 | 70-100 |
| Width (mm) | | | | |
| mean | 85.5 | 85 | 76.1 | 71.5 |
| range | 70-100 | 70-100 | 60-85 | 65-80 |
| Mid-tier leaf Length (mm) | | | | |
| mean | 269 | 265 | 281 | 211 |
| range | 217-311 | 225-313 | 205-341 | 150-298 |
| Width (mm) | | | | |
| mean | 132 | 133 | 156 | 122 |
| range | 115-150 | 110-145 | 140-170 | 90-175 |
| Leaf components | | | | |
| Petiole length (mm) | | | | |
| mean | 177 | 180 | 187 | 130 |
| range | 140-200 | 150-210 | 130-230 | 75-190 |
| Petiole diameter (mm) | | | | |
| mean | 3.8 | 3.8 | 3.6 | 3.6 |
| range | 3-5 | 3-5 | 3-4 | 3-4 |
| Petiolule length (mm) | | | | |
| mean | 9.3 | 6.4 | 6.9 | 6.3 |
| range | 7-11 | 5-8 | 5-9 | 5-8 |
| # leaflets/leaf | 3 | 3, rarely 4 or 5 | 3 | 3, rarely 4 |
| Leaf convexity | flat-convex, most slightly concave | very concave | flat to very concave | concave to very concave |
| Serrations | | | | |
| number/leaf | 19.1 | 20.8 | 20.3 | 18.9 |
| range | 18-20 | 16-26 | 17-26 | 12-22 |

TABLE 1-continued

Foliar and plant characteristics for 'Palomar', 'Camarosa', 'Camino Real', and 'Ventana'.

| Foliar Character | Cultivar 'Camarosa' | 'Camino Real' | 'Ventana' | 'Palomar' |
|---|---|---|---|---|
| shape | rounded, some semi-pointed | semi-pointed | semi-pointed | semi-pointed |
| Leaf pubescence | light-moderate | light-moderate | moderate-light | moderate |
| Petiole pubescence | | | | |
| density | heavy | moderate-heavy | heavy | moderate-heavy |
| direction | perpendicular | perpendicular to acropetal | perpendicular | perpendicular |
| Petiole color (Munsell) | 5 GY 8/8 | 5 GY 8/8 | 7.5 GY 8/7 | 5 GY 8/8 |
| Stipule length (mm) | | | | |
| mean | 17.6 | 19.1 | 19.4 | 18.7 |
| range | 10-24 | 15-25 | 15-25 | 12-23 |
| Stipule color | | | | |
| core | 7.5 GY 8/7 | 2.5 GY 5/5 | 2.5 GY 6/8 | 5 GY 8/8 |
| margins | 2.5 GY 8/9 | 2.5 GY 4/3 | 2.5 GY 6/8 | 2.5 GY 6/8 |
| Stolon base diameter (mm) | 3 | 3 | 2.4 | 2.6 |
| Stolons per nursery mother plant | 42.6 | 33.7 | 23.7 | 36.7 |
| Venation | | | | |
| pattern | pinnate | pinnate | pinnate | pinnate |
| color | 5 GY 4/3 | 7.5 GY 4/3 | 2.5 GY 4/3 | 5 GY 4/3 |

Disease and pest reaction: 'Palomar' is moderately resistant to powdery mildew (*Sphaerotheca macularis*), Anthracnose crown rot (*Colletotrichum acutatum*), and *Verticillium* wilt (*Verticillium dahliae*); it is moderately susceptible to *Phytophthora* crown rot (*Phytophthora cactorum*) and common leaf spot (*Ramularia tulasnei*) (Table 2). When treated properly, it has tolerance to two-spotted spider mites (*Tetranychus urticae*) equal to that for the comparison cultivars. 'Palomar' is tolerant to strawberry viruses encountered in California.

TABLE 2

Disease resistance scores for 'Palomar' and three comparison cultivars; *Phytophthora* and *Verticillium* scores were obtained in evaluations conducted in 2004-2006, *Colletotrichum* was evaluated in 2005-2006.

| Genotype | *Phytophthora* Resistance Score (5 = best) | *Verticillium* Resistance Score (5 = best) | *Colletotrichum* Resistance Score (5 = best |
|---|---|---|---|
| 'Camarosa' | 3.6 | 2.5 | 2.6 |
| 'Camino Real | 4.4 | 4.2 | 3.1 |
| 'Ventana' | 2.5 | 3.0 | 3.0 |
| 'Palomar' | 2.4 | 3.3 | 3.2 |

Flowering, fruiting, fruit and production characteristics: 'Palomar' is similar to other California short-day strawberry cultivars (e.g., 'Ventana', 'Camarosa', and 'Camino Real') in that it will flower over an extended period and into spring or summer, given appropriate local temperature and horticultural conditions. With very early plantation establishment (before October 1 in California) 'Palomar' produces fruit earlier than the comparison cultivars but with greater within-season variation than 'Ventana'. With later plantation establishment 'Palomar' initiates fruit later than 'Ventana' and is similar in production timing to 'Camino Real' and 'Camarosa'. Comparative statistics for flower and fruit characters near mid-season are given for the four cultivars in Table 3. The primary flowers for 'Palomar' are similar in size to the comparison cultivars with a calyx that is distinctly larger than the corolla on primary fruit; the sepals are similar in length and shape to 'Camarosa' and 'Ventana', but less wide than for 'Camino Real'. The calyx for 'Palomar' varies in position but is usually neither indented nor extended on the neck of the fruit; each primary flower has 5–7 petals. The petals are white on the upper and lower surfaces. The fruit shape for 'Palomar' can vary but is typically a short and symmetrical conic. It is easily distinguished by fruit shape from 'Camarosa' (shortened and flattened conic) or 'Ventana' (long conic); 'Palomar' usually has a greater proportion of symmetrical fruit than the comparison cultivars. External and internal fruit color for 'Palomar' is lighter than for 'Camarosa' and much lighter than for 'Camino Real', similar in color to 'Ventana' (Table 4). Achenes vary from yellow to dark red, and are even with the fruit surface or slightly indented (Table 6).

TABLE 3

Flower and fruit characters for 'Palomar' and three comparison cultivars.

| Character | Cultivar: 'Camarosa' | 'Camino Real' | 'Ventana' | 'Palomar' |
|---|---|---|---|---|
| Petal number | | | | |
| mean | 5.5 | 6.4 | 6.3 | 5.8 |
| range | 5-7 | 5-7 | 5-7 | 5-7 |
| Petal shape | | | | |
| apex | truncate to slightly obtuse | truncate to slightly obtuse | truncate to slightly obtuse | truncate to slightly obtuse |
| base | attenuate | attenuate | attenuate | attenuate |
| margin | entire | entire | entire | entire |
| Petal length (mm) | | | | |
| mean | 15.2 | 17.7 | 18.5 | 16.4 |
| range | 7-19 | 15-20 | 15-20 | 15-19 |
| Petal width (mm) | | | | |
| mean | 14.1 | 17.3 | 18.8 | 17.4 |
| range | 7-16 | 15-20 | 16-20 | 15-20 |
| Flower position (relative to foliage) | most even some exposed | exposed | even to exposed | even to exposed |
| Calyx diam.(mm) | | | | |
| mean | 57.5 | 58.5 | 58 | 59 |
| range | 40-70 | 50-70 | 48-70 | 50-70 |
| Corolla diam.(mm) | | | | |
| mean | 43.1 | 45.6 | 55.1 | 44.3 |
| range | 30-52 | 39-55 | 43-67 | 38-53 |
| Sepal length (mm) | | | | |
| mean | 24 | 24.5 | 23 | 25.1 |

TABLE 3-continued

Flower and fruit characters for 'Palomar' and three comparison cultivars.

| Character | Cultivar: 'Camarosa' | 'Camino Real' | 'Ventana' | 'Palomar' |
|---|---|---|---|---|
| range | 13-30 | 20-35 | 20-25 | 20-30 |
| Sepal width (mm) | | | | |
| mean | 12.8 | 15.3 | 11.1 | 12.8 |
| range | 5-20 | 8-20 | 8-15 | 10-17 |
| Sepal color (Munsell) | 2.5 GY 5/5 | 5 GY 5/6 | 5 GY 6/8 | 5 GY 5/6 |
| Pedicel length (mm) | | | | |
| mean | 130 | 85 | 129 | 128 |
| range | 110-150 | 70-110 | 100-150 | 110-150 |
| Pedicel diameter (mm) | | | | |
| mean | 3.7 | 3 | 3.7 | 3.7 |
| range | 3-4.5 | 2-4 | 3-5 | 3-4.5 |
| Pedicel color | 5 GY 6/8 | 2.5 GY 6/8 | 5 GY 5/6 | 5 GY 8/8 |
| Fruit shape | | | | |
| Fruit length (mm) | | | | |
| mean | 85 | 68 | 72.2 | 71.7 |
| range | 50-130 | 50-100 | 60-100 | 52-91 |
| Fruit width (mm) | | | | |
| mean | 70 | 62 | 63.3 | 64.2 |
| range | 50-100 | 40-90 | 50-80 | 52-81 |
| Length/width | | | | |
| ratio | 1.2 | 1.1 | 1.2 | 1.1 |
| range | 0.7-2.1 | 0.8-1.4 | 0.9-1.4 | 0.9-1.3 |
| subjective | Obovate-flat | Short conic | Medium conic | Short conic |
| Primary/ secondary fruit comparison | | | | |
| size (subjective) | 40-60% | 70-80% | 50-60% | 50-60% |
| shape | similar shape, more conic | similar shape | similar shape | similar shape |
| Extent/size of hollow core | small-absent | absent | small | small-absent |
| Calyx | | | | |
| position | indented-neck | even-indented | even-reflexed | even-indented |
| size relative to fruit | equal or less than fruit diameter | equal or greater than fruit diameter | equal or less than fruit diameter | equal or greater than fruit diameter |
| Seed position | indented-extruded | even-indented | even-extruded | even-indented |
| Adherence of Calyx to Fruit | weak | strong | intermediate | weak |

Flower measurements obtained on Mar. 21, 2005, fruit measurements on May 9, 2005.

TABLE 4

Foliar and fruit color characteristics for 'Palomar' and three comparison cultivars.

| Color Character | Cultivar 'Camarosa' | 'Camino Real' | 'Ventana' | 'Palomar' |
|---|---|---|---|---|
| Leaf color (CIELAB) Adaxial | | | | |
| L* | | | | |
| mean | 34.5 | 29.7 | 33.8 | 32.2 |
| range | 31.6-37.9 | 27.3-31.5 | 31.4-35.9 | 30.6-34.9 |
| a* | | | | |
| mean | −11 | −8 | −11.2 | −9.5 |
| range | −9.2--12.4 | −6.3--9.9 | −9.1--13.7 | −8.5--11.2 |
| b* | | | | |
| mean | 16.7 | 10.2 | 15.5 | 12.4 |
| range | 12.8-18.5 | 8.2-12.5 | 12.4-19.7 | 10.9-15.0 |
| Munsell | 5 GY 4/3 | 5 GY 4/3 | 5 GY 5/6 | 5 GY 4/3 |
| Abaxial | | | | |
| L* | | | | |
| mean | 50.8 | 48 | 40 | 49.8 |
| range | 48.6-52.7 | 47.6-49.0 | 46.8-51.5 | 47.2-52.3 |
| a* | | | | |
| mean | −9.4 | −9.4 | −9 | −9.3 |
| range | −7.9--10.6 | −8.2--10.1 | −8.0--9.8 | −8.0--9.8 |
| b* | | | | |
| mean | 19.4 | 16.4 | 17.7 | 15.7 |
| range | 17.0-22.3 | 15.0-18.1 | 15.4-21.3 | 13.8-16.9 |
| Munsell | 5 GY 6/8 | 5 GY 6/8 | 7.5 GY 7/9 | 5 GY 7/10 |
| Fruit color (CIELAB) External | | | | |
| L* | | | | |
| mean | 39.2 | 33.7 | 38.4 | 39.3 |
| range | 37.1-42.4 | 29.0-39.4 | 34.4-42.9 | 36.5-44.8 |
| a* | | | | |
| mean | 40.6 | 36.4 | 40.5 | 43.1 |
| range | 35.8-43.5 | 31.4-41.2 | 33.5-46.5 | 38.1-47.9 |
| b* | | | | |
| mean | 25.6 | 20.2 | 25.7 | 27.4 |
| range | 22.1-28.9 | 13.6-27.5 | 19.7-29.5 | 21.7-34.1 |
| Munsell | 7.5 R3/6 | 5 R 3/7 | 5 R 3/7 | 7.5 R 4/11 |
| Internal | | | | |
| L* | | | | |
| mean | 60.4 | 56.6 | 61.4 | 59.1 |
| range | 53.9-67.8 | 49.2-61.6 | 54.7-68.8 | 46.5-64.1 |
| a* | | | | |
| mean | 35.4 | 36.3 | 33.1 | 29.3 |
| range | 27.4-43.4 | 29.7-41.2 | 23.7-39.5 | 22.9-36.4 |
| b* | | | | |
| mean | 36.3 | 35.8 | 34.1 | 30.9 |
| range | 27.4-45.7 | 30.6-40.9 | 27.6-40-2 | 24.3-37.4 |
| Munsell | 7.5 R 4/11 | 7.5 R 5/13 | 7.5 R 6/12 | 7.5 R 7/9 |
| Achene color | | | | |
| Munsell | 7.5 R 3/6 | 5 R 3/7 | 5 R 4/12 | 5 R 3/7 |

*CIELAB is the abbreviation of the international color system known as "Commission Internationale de l'Eclairage" 1978. For recommendations concerning uniform color spaces, color difference equations, and psychometric color terms see Supplement No. 2 of CIE Publication No. 15, Paris.

'Palomar' has been tested under a variety of cultural regimes, and optimal performance is obtained when nursery treatments and nutritional programs similar to those for 'Camarosa', 'Ventana', and 'Camino Real' are used. In general, 'Palomar' is less vigorous than 'Camarosa' or 'Ventana' with very early season planting is less sensitive to excess chilling than 'Ventana'. 'Palomar' retains excellent fruit quality in summer planting systems.

When treated with appropriate planting regimes, 'Palomar' has larger fruit and produces individual-plant yields to similar to that of 'Camarosa'; it produces less fruit per plant but develops larger and higher quality fruit than 'Ventana' (Table 5). 'Palomar' has a similar production pattern to 'Camino Real' with most cultural treatments, although the production is less peaked and it is substantially more adapted to early-season winter planting. Commercial appearance ratings have been better than those for all of the comparison cultivars, especially 'Camarosa'; those superior appearance scores translate directly into a larger fraction of marketable fruit than is produced by the comparison cultivars. Fruit for 'Palomar' is substantially firmer than fruit from 'Ventana', similar in firmness to the other comparison cultivars. Subjectively, 'Palomar' has outstanding flavor. The fruit will be exceptional for both fresh market and processing, and will be useful for home garden purposes.

TABLE 5

Performance of 'Palomar' and three comparison cultivars evaluated at the Watsonville Research Facility in 2004-6. All plants for these trials were harvested from a commercial nursery near Macdoel, CA on October 15-16, and transplanted after 6-15 days supplemental storage. Fruit harvest was initiated in early April and continued through the last week of August. (52" 2-row beds, 17,300 plants/acre).

| Item | Yield (g/plant) | Appearance Score (5 = best) | Fruit Size (g/fruit) | Firmness* |
|---|---|---|---|---|
| 'Camarosa' | 2,086 | 3.1 | 26.1 | 9.9 |
| 'Camino Real' | 2,086 | 3.5 | 31.3 | 9.8 |
| 'Ventana' | 2,331 | 3.4 | 30.6 | 8.8 |
| 'Palomar' | 2,031 | 3.7 | 30.2 | 10.2 |

*Fruit firmness ratings are the amount of force in tenths of pounds required to drive a 3 mm flat probe 1 cm into a ripe fruit. This is measured with a Hunter Force Guage.

TABLE 6

Achenes number per fruit and size for 'Palomar' and three comparison cultivars.

| Cultivar | Sample | Weight (g) | Seed Count | Seed/g | Achene Size (mm) |
|---|---|---|---|---|---|
| 'Camarosa' | 1 | 45 | 427 | 9.49 | |
| | 2 | 47 | 577 | 12.28 | |
| | 3 | 47 | 502 | 10.68 | |
| | Average | 46.33 | 502.00 | 10.82 | 1.3 × 1.7 |
| 'Ventana' | 1 | 44 | 441 | 10.02 | |
| | 2 | 41 | 471 | 11.49 | |
| | 3 | 54 | 491 | 9.09 | |
| | Average | 46.33 | 467.67 | 10.20 | 1.2 × 1.6 |
| 'Camino' | 1 | 42 | 371 | 8.83 | |
| | 2 | 45 | 470 | 10.44 | |
| | 3 | 38 | 447 | 11.76 | |
| | Average | 41.67 | 429.33 | 10.35 | 1.3 × 1.75 |
| 'Palomar' | 1 | 38 | 463 | 12.18 | |
| | 2 | 36 | 458 | 12.72 | |
| | 3 | 29 | 450 | 15.52 | |
| | Average | 34.33 | 457.00 | 13.47 | 1.2 × 1.4 |

* The seed count is the number of seed per fruit. The seed/g is the number of seeds per gram of fresh fruit weight because the fruit size differs. The averages may vary depending on culture conditions and regimen.

What is claimed is:

1. A new and distinct cultivar of strawberry plant having the characteristics substantially as described and illustrated herein.

* * * * *